United States Patent [19]

Meier et al.

[11] Patent Number: 5,008,392

[45] Date of Patent: Apr. 16, 1991

[54] PROCESS FOR THE PREPARATION OF PYRIDINE-2,3-DICARBOXYLIC ACID ESTERS

[75] Inventors: Josef Meier; Wolfgang Deinhammer; Konrad Krageloh, all of Burghausen, Fed. Rep. of Germany

[73] Assignee: Wacker-Chemie GmbH, Munich, Fed. Rep. of Germany

[21] Appl. No.: 441,367

[22] Filed: Nov. 27, 1989

[30] Foreign Application Priority Data

Dec. 1, 1988 [DE] Fed. Rep. of Germany ....... 3840554

[51] Int. Cl.$^5$ .......................................... C07D 213/803
[52] U.S. Cl. ...................................................... 546/250
[58] Field of Search ........................................... 546/250

[56] References Cited

U.S. PATENT DOCUMENTS

| | | | |
|---|---|---|---|
| 2,724,714 | 11/1955 | Jones | 546/250 |
| 4,723,011 | 2/1988 | Doehner | 546/250 |
| 4,871,859 | 10/1989 | Gupton et al. | 546/250 |
| 4,948,896 | 8/1990 | Nagao | 546/250 |

FOREIGN PATENT DOCUMENTS

| | | | |
|---|---|---|---|
| 0274379 | 7/1988 | European Pat. Off. | 546/250 |
| 1139566 | 6/1989 | Japan | 546/250 |

OTHER PUBLICATIONS

March, *Advanced Organic Chemistry*, 3rd edition, 1985, Wiley and Sons, pp. 364–365.

*Primary Examiner*—Robert W. Ramsuer
*Assistant Examiner*—Lenora Miltenberger
*Attorney, Agent, or Firm*—Collard, Roe & Galgano

[57] ABSTRACT

The invention relates to a process for the preparation of pyridine-2,3-dicarboxylic acid esters using novel maleic acid esters as starting materials. In the process, in a first process step, 2,3-dihalomaleic acid esters are reacted with ammonia, or ammonium salts, with the exclusion of water at a temperature of at least 50° C. to form novel 2-amino-3-halomaleic acid esters, and these are subsequently reacted further in a second process step with $\alpha,\beta$-unsaturated aldehydes, or ketones, in the presence of an acidic catalyst and acid-binding agents at a temperature of at least 50° C. with heat being supplied until the pyridine-2,3-dicarboxylic acid esters have been formed. Pyridine-2,3-dicarboxylic acid esters of this type can be used, for example, as intermediates for synthesis of herbicides based on imidazoline. The present invention also relates to novel 2-amino-3-halomaleic acid esters, which are useful for producing the final product pyridine-2,3-dicarboxylic acid esters.

5 Claims, No Drawings

PROCESS FOR THE PREPARATION OF PYRIDINE-2,3-DICARBOXYLIC ACID ESTERS

BACKGROUND OF THE INVENTION

1. Field of the Invention

The invention relates to a process for the preparation of pyridine-2, 3-dicarboxylic acid esters using novel maleic acid esters as the starting materials. The pyridine-2, 3-dicarboxylic acid esters, which may optionally be substituted in the 4-, 5- or 6- position, are themselves valuable intermediates for syntheses of herbicidally-active 2-(2-imidazolin-2-yl) -pyridine-3-carboxylic acid derivatives, as described in EP-B-41,623. Also the present invention relates to novel 2-amino-3-halomaleic acid esters, which are useful for producing the final product pyridine-2,3-dicarboxylic acid esters.

2. The Prior Art

The following processes are known for the preparation of pyridine-2, 3-dicarboxylic acid esters:

1. Reaction of $\alpha,\beta$-unsaturated N, N-dialkylhydrazones with halomaleic acid derivatives to form 1-amino-1, 4-dihydropyridine-2, 3, dicarboxylic acid derivatives and subsequent treatment (thermal or acid treatment), the desired pyridine derivatives being produced with elimination of amine, as described in EP-A-161,221.

2. Reaction of $\alpha,\beta$-unsaturated aldehydes or ketones with $\alpha$-halo-$\beta$-keto esters in the presence of ammonium salts, as described in DE-A-3,634,975, and 3. Reaction of $\beta$-alkynyl-ketones with aminomaleates or aminofumarates to form pyridine-2,3-dicarboxylic acid esters which are substituted exclusively in the 6-position; 5, 6-dimethylpyridine-2,3-dicarboxylic acid esters can in contrast be obtained by reacting 4-dimethyl-amino-3-methyl-butenone with amino fumarate, as described in GB-A-2,174,395.

Process (1) has the disadvantage that carcinogenic hydrazine derivatives are employed and the synthesis extends over several steps. In process (2), halooxalacetic esters which are not readily available are employed. These can be prepared by Claisen condensation of haloacetic esters and oxalic acid esters in moderate yields. Similarly, process (3) requires alkinyl ketones or alkenyl ketones containing terminal dimethylamino groups, which are likewise not readily accessible.

SUMMARY OF THE INVENTION

It is an object of the present invention to provide a process for the preparation of 2,3-pyridine carboxylic acid esters which may be substituted in the 4-, 5-and/or 6- position which, proceeding from readily accessible starting materials, gives intermediates which, for example, are important for herbicide synthesis, in good yields in a simple and inexpensive manner.

The above object is accomplished in accordance with the present invention by providing for the preparation of pyridine-2, 3-dicarboxylic acid esters of the formula

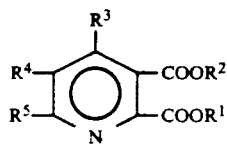

(I)

in which $R^1$ and $R^2$, which may be identical or different, are alkyl having 1 to 8 carbon atoms and $R^3$, $R^4$ and $R^5$, which may be identical or different, are hydrogen atoms, alkyl having 1 to 8 carbon atoms or phenyl, by a process comprising, in a first process step, (a) reacting a 2, 3-dihalomaleic acid ester of the formula

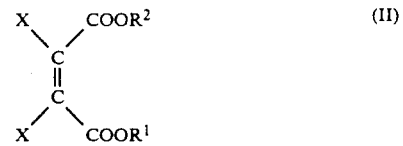

(II)

in which $R^1$ and $R^2$ are as defined above and X is halogen, with ammonia, or an ammonium salt, in the presence of an organic solvent with the exclusion of water at a temperature of at least 50° C., to produce a 2-amino-3-halomaleic acid ester of the formula

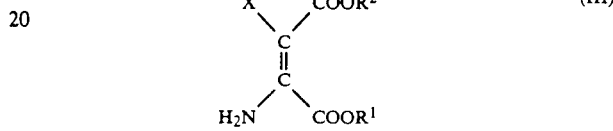

(III)

in which $R^1$, $R^2$, and X are as defined above, and (b) reacting said 2-amino-3-halomaleic acid ester of the above formula (III) in a second process step, with $\alpha,\beta$-unsaturated aldehydes or ketones of the formula

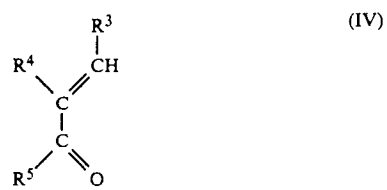

(IV)

in which $R^3$, $R^4$ and $R^5$ are as defined above, in the presence of an acidic catalyst, an organic solvent and an acid-binding agent, at a temperature of at least 50° C. to produce the ester (I).

The present invention is furthermore directed to novel 2-amino-3-halomaleic acid esters of the formula

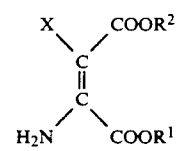

in which $R^1$ and $R^2$, which may be identical or different, are straight-chain, or branched, alkyl having 1 to 8 carbon atoms and X is halogen.

Other objects and features of the present invention will become apparent from the following detailed description considered in connection with the accompanying examples which disclose various embodiments of the present invention. It should be understood, however, that the examples are presented for the purpose of illustration only and not as a definition of the limits of the invention.

DETAILED DESCRIPTION OF PREFERRED EMBODIMENTS

Examples of radicals $R^1$ and $R^2$ in the compounds of the formulae (I), (II) and (III) are alkyl radicals which, as defined, have up to 8 carbon atoms and may be straight-chain or branched, such as methyl, ethyl, n-propyl, iso-propyl, n-butyl, iso-butyl, pentyl, hexyl, heptyl and octyl radicals. Alkyl radicals having 1-4 carbon atoms are preferred due to the ready availability.

Examples of radicals $R^3$, $R^4$ and $R^5$ in the compounds of the formulae (I) and (IV) are, apart from hydrogen atoms and phenyl radicals, the same alkyl radicals as indicated for $R^1$ and $R^2$.

Examples of radicals X in the compounds of the formulae (II) and (III) are halogen atoms, preferably chlorine or bromine atoms.

The compounds (II) and (IV) are known and can be prepared by known processes.

To carry out the process according to the invention, the dihalomaleic acid esters (II) are reacted in the first process step (a), as defined, with ammonia or ammonium salts at temperatures in the range from 50° C. to 150° C., preferably from 60° C. to 120° C., under anhydrous conditions. The reaction media used are advantageously aprotic solvents. Examples of these are carboxamides, such as dimethylformamide and dimethylacetamide. However, it is also possible to use alkanols, such as methanol, ethanol, propanol or butanol. When ammonia is used, it is advantageously passed into the reaction mixture preheated to the reaction temperature in the form of dry gaseous ammonia until the exothermic reaction is virtually complete. The reaction medium used is advantageously dimethylformamide, containing catalytic amounts of an acid, preferably anhydrous acetic acid. When ammonium salts are used, at least 2 moles, preferably 2.5 moles, of the ammonium salt are employed per mole of (II). Dimethylformamide or dimethylacetamide, in particular, have proven suitable as the reaction medium. Examples of ammonium salts are ammonium acetate, ammonium formate and ammonium sulphamate, ammonium acetate being preferred. The reaction mixture is preheated to the reaction temperature, it being possible to ensure good distribution of the reactants by mechanical agitation. The reaction time is generally dependent on the amounts of starting materials employed. When the reaction is complete and the solvent has subsequently been removed, the 2-amino-3-halomaleic acid esters (III) are obtained.

These compounds are novel and are not yet described in the literature. At room temperature, they are viscous liquids with a reddish coloration, or crystals with a yellowish coloration. The compounds (III) obtained in this way can be washed with water and/or be recrystallized after the solvent has been removed. However, they can also be employed directly, i.e. without further purification, for the next process step (b).

In the second process step (b), the aminohalomaleic acid esters (III) are reacted, as defined, with α,β-unsaturated aldehydes or ketones (IV) to form the desired pyridine derivatives (I) at temperatures in the range from 50° C. to the boiling point of the solvent, preferably from 70° C. to 110° C.

Examples of organic solvents which can be used as reaction medium are alkanols, chlorohydrocarbons, hydrocarbons, ethers, carboxylic acids and esters thereof, carboxylic acid nitriles and carboxamides, such as acetonitrile and dimethylformamide. Acid-binding agents advantageously employed are pyridine, picolines, N,N-dialkylanilines, ammonium acetates and alkali metal acetates, pyridine having proved particularly suitable. Acid catalysts which are preferably used are carboxylic acids, in particular anhydrous acetic acid.

The reactants (III) and (IV) and the acid-binding agents are employed in approximately equimolar amounts and component (IV) is preferably used in a slight excess (1.1 moles per mole of III). The use of anhydrous acetic acid, which simultaneously serves as solvent and catalyst, has proved particularly suitable. When the reaction is complete, which, in general, may take several hours with heat being continuously supplied, the pyridine derivatives (I) are isolated by customary techniques, such as extraction, evaporation or column chromatography.

The invention will now be explained more fully in the following examples which are, however, only given by way of illustration and not of limitation.

EXAMPLE 1

53.25 g (0.25 mol) of dimethyl dichloromaleate were dissolved in 100 ml of dimethylformamide, and 48.16 g (0.625 mol) of ammonium acetate were added. The mixture was rapidly heated to 120° C. and stirred at 110° C. to 120° C. for one hour. The solvent was subsequently removed by distillation, the residue was taken up in methylene chloride, and the solution was washed with water. The methylene chloride was removed by distillation on an evaporator, and, after recrystallization, 40 g (83% yield) of dimethyl aminochloromaleate were obtained in the form of yellowish, cubic crystals (m.p. 96°–98° C.)

NMR spectra: δ values in CDCl₃:

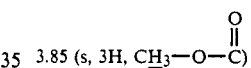

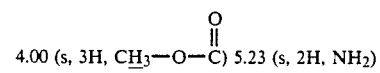

EXAMPLE 2

48.2 g (0.2 mol) of diethyl dichloromaleate were dissolved in 80 ml of dimethylformamide and 2 ml of glacial acetic acid, and the mixture was warmed to 100° C. Ammonia gas was then passed in. During this operation, the temperature increased to about 120° C. After 30 minutes, the temperature dropped back to 100° C.; the reaction was then complete. The solvent was then removed by vacuum distillation. The residue was taken up in methylene chloride, and the solution was washed with water. The methylene chloride solution was evaporated in a rotary evaporator. 38.9 g (87.8% yield) of diethyl aminochloromaleate were obtained as a yellow oil which solidified on trituration to form needle-shaped crystals (m.p. 84° C.–86° C.).

¹H NMR spectra: δ values in CDCl₃:

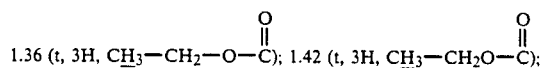

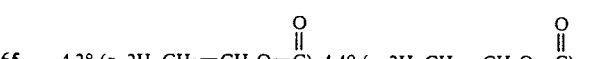

EXAMPLE 3

26.9 g (0.1 mol) of dipropyl dichloromaleate, 19.27 g (0.25 mol) of ammonium acetate and 40 ml of dimethylformamide were reacted under the same conditions as described in Example 1. 24.1 g (87.4% yield) of dipropyl aminochloromaleate were obtained as a reddish, viscous liquid (purity according to GC analysis 90.5%)

$^1$H NMR spectra: δ values in CDCl$_3$:

0.88 (t, 3H, C$\underline{H}_3$—CH$_2$—CH$_2$); 0.92 (t, 3H, C$\underline{H}_3$—CH$_2$—CH$_2$);

1.51 (m$_c$, 2H, CH$_3$—C$\underline{H}_2$—CH$_2$); 1.67 (m$_c$, 2H, CH$_3$—C$\underline{H}_2$—CH$_2$);

4.05 (t, 2H, $\overset{O}{\overset{\|}{C}}$—OC$\underline{H}_2$—CH$_2$—); 4.15 (t, 2H, $\overset{O}{\overset{\|}{C}}$—OC$\underline{H}_2$—CH$_2$);

5.70 (s, 2H, NH$_2$).

EXAMPLE 4

29.7 g (0.1 mol) of dibutyl dichloromaleate, 19.27 g (0.25 mol) of ammonium acetate and 40 ml of dimethylformamide were reacted under the same conditions as described in Example 1. 27.55 g (88.7% yield) of dibutyl aminochloromaleate were obtained as a reddish, viscous liquid (purity according to GC analysis 90%).

$^1$H NMR spectrum: δ values in CDCl$_3$:

0.93 (m$_c$, 6H, 2x C$\underline{H}_3$—CH$_2$—CH$_2$—);

1.42 (m$_c$, 4H, 2x CH$_3$—C$\underline{H}_2$—CH$_2$—)

1.75 (m$_c$, 4H, 2x CH$_3$—CH$_2$—C$\underline{H}_2$—CH$_2$—$\overset{O}{\overset{\|}{C}}$—), 4.13 (t, 2H, $\overset{O}{\overset{\|}{C}}$—OC$\underline{H}_2$—CH$_2$—)

4.25 (t, 2H, $\overset{O}{\overset{\|}{C}}$—OC$\underline{H}_2$—CH$_2$—); 5.53 (s, 2H, —NH$_2$).

EXAMPLE 5

26.9 g (0.1 mol) of diisopropyl dichloromaleate, 19.27 g (0.25 mol) of ammonium acetate and 40 ml of dimethylformamide were reacted under the same conditions as described in Example 1. 29.65 g (85.6% yield) of diisopropyl aminochloromaleate were obtained as a reddish-yellow, viscous liquid (purity according to GC analysis 83%).

$^1$H NMR spectrum: δ values in CDCl$_3$:

1.31 (d, 6H, $\overset{O}{\overset{\|}{C}}$—OCH(C$\underline{H}_3$)$_2$); 1.39 (d, 6H, $\overset{O}{\overset{\|}{C}}$—OCH(C$\underline{H}_3$)$_2$);

5.16 (h, 1H $\overset{O}{\overset{\|}{C}}$—OC$\underline{H}$(CH$_3$)$_2$); 5.30 (h, 1H, $\overset{O}{\overset{\|}{C}}$—OC$\underline{H}$(CH$_3$)$_2$);

5.65 (s, 2H, NH$_2$)

EXAMPLE 6

29.7 g (0.1 mol) of diisobutyl dichloromaleate, 19.27 g (0.25 mol) of ammonium acetate and 40 ml of dimethylformamide were reacted under the same conditions as described in Example 1. A reddish oil was obtained which crystallized on trituration. After the crystal slurry had been washed with hexane, 22.3 g (80%) of diisobutyl aminochloromaleate were obtained as cubic crystals (m.p. 80° C.-81° C.).

$^1$H NMR Spectrum: δ values in CDCl$_3$:

0.95 (d, 6H, CH$_2$—CH(C$\underline{H}_3$)$_2$; 0.98 (d, 6H, —CH$_2$—CH(C$\underline{H}_3$)$_2$);

2.02 (m$_c$, 2H, 2x —CH$_2$—C$\underline{H}$—(CH$_3$)$_2$);

3.95 (d, 2H, $\overset{O}{\overset{\|}{C}}$—OC$\underline{H}_2$—CH(CH$_3$)$_2$);

4.05 (d, 2H, $\overset{O}{\overset{\|}{C}}$—OC$\underline{H}_2$—(CH(CH$_3$)$_2$); 5.02 (s, 2H, NH$_2$).

EXAMPLE 7

A stirred mixture of 22.16 g (0.1 mol) of diethyl aminochloromaleate, 8.92 g (0.105 mol.) of ethyl acrolein, 8.3 g (0.105 mol) of pyridine and 1 ml of glacial acetic acid in 25 ml of ethanol was refluxed. After five hours, the mixture was cooled to room temperature, and the solvent was removed under reduced pressure.

The residue was taken up in methylene chloride, and the solution was washed with water. The solvent was subsequently removed in a vacuum. 25.8 g (80% yield) of diethyl 5-ethylpyridine-2,3-dicarboxylate were obtained as a reddish, viscous oil. According to a gas chromatography analysis, the product was 81% pure.

EXAMPLES 8 TO 20

The process of Example 7 was repeated under the same conditions, with various aminochloromaleates of the formula (III) being reacted with ethyl acrolein, methyl acrolein and acrolein. The 5-substituted pyridine-2,3-dicarboxylates indicated in Table I below were obtained:

TABLE I

| Example No. | R$^1$ | R$^2$ | R$^4$ | Yield | Analysis |
|---|---|---|---|---|---|
| 8 | CH$_3$ | CH$_3$ | CH$_3$ | 48 | $^1$H NMR; GC |
| 9 | CH$_3$ | CH$_3$ | C$_2$H$_5$ | 65 | $^1$H NMR; GC |
| 10 | C$_2$H$_5$ | C$_2$H$_5$ | CH$_3$ | 72 | $^1$H NMR; GC |
| 11 | C$_2$H$_5$ | C$_2$H$_5$ | H | 35 | $^1$H NMR; GC |
| 12 | n-C$_3$H$_7$ | n-C$_3$H$_5$ | C$_2$H$_5$ | 70 | $^1$H NMR; GC |
| 13 | n-C$_3$H$_7$ | n-C$_3$H$_7$ | CH$_3$ | 56 | $^1$H NMR; GC |
| 14 | i-C$_3$H$_7$ | i-C$_3$H$_7$ | C$_2$H$_5$ | 81 | $^1$H NMR; GC |
| 15 | i-C$_3$H$_7$ | i-C$_3$H$_7$ | H | 36 | $^1$H NMR; GC |
| 16 | n-C$_4$H$_9$ | n-C$_4$H$_9$ | C$_2$H$_5$ | 77 | $^1$H NMR; GC |
| 17 | n-C$_4$H$_9$ | n-C$_4$H$_9$ | H | 36 | $^1$H NMR; GC |
| 18 | i-C$_4$H$_9$ | i-C$_4$H$_9$ | C$_2$H$_5$ | 68 | $^1$H NMR; GC |
| 19 | i-C$_4$H$_9$ | i-C$_4$H$_9$ | CH$_3$ | 48 | $^1$H NMR; GC |
| 20 | C$_2$H$_5$ | C$_2$H$_5$ | n-C$_3$H$_7$ | 84 | $^1$H NMR; GC |

The effectiveness of various solvents and bases in the preparation of diethyl 5-ethylpyridine-2,3-dicarboxylate was tested as follows:

Diethyl aminochloromaleate was reacted with ethyl acrolein and with various bases in various solvents in accordance with the procedure of Example 7 to give diethyl-5-ethyl-pyridine-2,3-dicarboxylate. The results of the experiments are collated in Table (II). From this Table the effectiveness of the various bases and solvents in the process according to the invention can be seen.

TABLE II
Effectiveness of bases and solvents

| Base | Solvent | Yield of 5-ethyl-pyridine-2, 3-dicarboxylate |
|---|---|---|
| NH₄OAc | EtOH* | 37% |
| NEt₃ | EtOH | 5% |
| N,N-Dimethylaniline | EtOH | 48% |
| NaOAc | EtOH | 9% |
| Na-isobutyrate | Isobutyric acid | 22% |
| Pyridine | DMF** | 71% |
| Pyridine | Tri*** | 62% |
| Pyridine | Toluene | 58% |
| Pyridine | Cyclohexane | 36% |
| Pyridine | Ethyl acetate | 9% |
| Pyridine | Acetonitrile | 15% |
| Pyridine | Diisopropyl ether | 16% |
| Pyridine | Methyl ethyl ketone | 62% |
| Pyridine | Isobutyric acid | 85% |
| Pyridine | Isobutanol | 75% |
| Pyridine | Acetone | 38% |
| Pyridine | Acetic acid | 88% |

*EtOH = ethanol
**DMF = dimethylformamide
***Tri = trichloroethylene

While only a few embodiments and examples of the present invention have been described, it is to be understood that many changes and modifications may be made thereunto without departing from the spirit and scope of the invention as defined in the appended claims.

What is claimed is:

1. A process for the preparation of a pyridine-2, 3-dicarboxylic acid ester of the formula

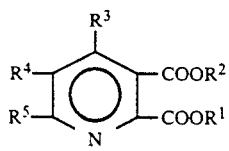

(I)

in which $R^1$ and $R^2$, which may be identical or different, are alkyl having 1 to 8 carbon atoms and $R^3$, $R^4$ and $R^5$, which may be identical or different, are hydrogen, alkyl having 1 to 8 carbon atoms or phenyl, comprising in a first process step, (a) reacting a 2,3-dihalomaleic acid ester of the formula

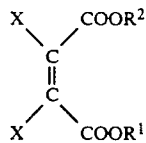

(II)

in which $R^1$ and $R^2$ are as defined above, and X is halogen with ammonia, or an ammonium salt, in the presence of an organic solvent with the exclusion of water, and at a temperature of at least 50° C., to produce a 2-amino-3-halomaleic acid ester of the formula

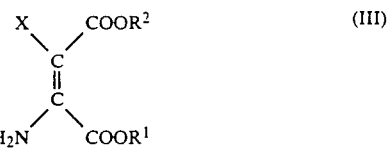

(III)

in which $R^1$, $R^2$ and X are as defined above, and (b) reacting said 2-amino-3-halomaleic acid ester of the above formula (III), in a second process step, with an α,β-unsaturated aldehyde, or ketone, of the formula

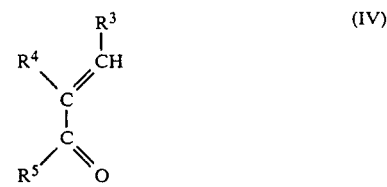

(IV)

in which $R^3$, $R^4$ and $R^5$ are as defined above, in the presence of an acidic catalyst, an organic solvent and an acid-binding agent, at a temperature of at least 50° C. to produce the ester (I).

2. The process as claimed in claim 1, wherein the reaction in the first process step (a) comprises preheating a reaction mixture, which comprises a reactant (II) and dimethylformamide containing catalytic amounts of anhydrous acetic acid, at temperatures in the range from 60° C. to 120° C.; and
passing dry gaseous ammonia into said preheated reaction mixture.

3. The process as claimed in claim 1, wherein the reaction in the first process step (a) comprises heating a reaction mixture which comprises reactant (II) and ammonium acetate in the molar ratio 1:2.5 and dimethylformamide at a temperature in the range from 60° C. to 120° C.

4. The process as claimed in claim 1, wherein the reaction in the second process step (b) comprises heating for several hours a reaction mixture which comprises reactants (III), (IV) and pyridine in the molar ratio from 1:1 to 1.1:1 and anhydrous acetic acid at a temperature in the range from 70° C. to 110° C.

5. The process as claimed in claim 1, wherein the reaction in the second process step (b) comprises heating for several hours a reaction mixture which comprises reactants (III), (IV) and pyridine in the molar ratio from 1:1 to 1.1:1 and isobutyric acid at a temperature in the range from 70° C. to 110° C.

* * * * *